US010849637B1

(12) United States Patent
Mantell (10) Patent No.: US 10,849,637 B1
(45) Date of Patent: Dec. 1, 2020

(54) ROUNDED INVASIVE ELECTROHYDRAULIC LITHOTRIPSY PROBE WITH PORTS

(71) Applicant: Northgate Technologies, Inc., Elgin, IL (US)

(72) Inventor: Robert R. Mantell, Arlington Heights, IL (US)

(73) Assignee: NORTHGATE TECHNOLOGIES, INC., Elgin, IL (US)

( * ) Notice: Subject to any disclaimer, the term of this patent is extended or adjusted under 35 U.S.C. 154(b) by 240 days.

(21) Appl. No.: 15/398,987

(22) Filed: Jan. 5, 2017

Related U.S. Application Data

(60) Provisional application No. 62/275,999, filed on Jan. 7, 2016.

(51) Int. Cl.
*A61B 18/26* (2006.01)
*A61B 17/22* (2006.01)
*A61B 17/00* (2006.01)

(52) U.S. Cl.
CPC ............ *A61B 17/22022* (2013.01); *A61B 2017/00942* (2013.01); *A61B 2017/22008* (2013.01); *A61B 2017/22025* (2013.01)

(58) Field of Classification Search
CPC ........ A61B 17/225–2258; A61B 17/22; A61B 17/22004–22032; A61B 17/221; A61B 18/26; A61B 2018/263–266; A61B 2017/2253
See application file for complete search history.

(56) References Cited

U.S. PATENT DOCUMENTS

| | | | | |
|---|---|---|---|---|
| 4,178,935 A | * | 12/1979 | Gekhman | A61B 17/22012 606/128 |
| 4,927,427 A | * | 5/1990 | Kriauciunas | A61B 17/22022 606/128 |
| 5,152,768 A | * | 10/1992 | Bhatta | A61B 17/22022 601/4 |
| 8,012,158 B2 | * | 9/2011 | Irion | A61B 17/22022 606/128 |
| 2004/0097963 A1 | * | 5/2004 | Seddon | A61B 17/22022 606/127 |
| 2010/0036294 A1 | * | 2/2010 | Mantell | A61B 17/22022 601/4 |

FOREIGN PATENT DOCUMENTS

WO   WO-2014140715 A2 *  9/2014  ....... A61B 17/22022

* cited by examiner

*Primary Examiner* — Anh T Dang
(74) *Attorney, Agent, or Firm* — Brinks Gilson & Lione (57) ABSTRACT

A lithotripter tip configured for use within an invasive lithotripter probe may include a lithotripter tip body defining an interior region in communication with an aperture at a distal end of the lithotripter tip body and defining at least one port in communication with the interior region. A first electrode and a second electrode are positioned within the interior region of the lithotripter tip such that such that when liquid is within the interior region and an electric arc occurs between the first and second electrodes, a gaseous bubble forms within the interior region and a resulting shockwave travels out of the aperture at the distal end of the lithotripter tip body.

11 Claims, 12 Drawing Sheets

ROUNDED INVASIVE ELECTROHYDRAULIC LITHOTRIPSY PROBE WITH PORTS

RELATED APPLICATION

The present application claims priority to U.S. Provisional Patent Appln. No. 62/275,999, filed on Jan. 7, 2016, the entirety of which is hereby incorporated by reference.

BACKGROUND

Electrohydraulic lithotripsy has been used in the medical field, primarily for breaking concretions in the urinary or biliary tract. The recent introduction of endoscopes, such as Boston Scientific's Spy Scope®, Olympus's Mother/Daughter Gastroscope, and ACMI's flexible ureteroscopes, that are designed to reach more remote locations in the body, such as the common duct, hepatic duct, kidney, ureter, and bladder, have increased the need for electrohydraulic lithotripsy probes that can more easily access remote locations in patients.

DETAILED DESCRIPTION OF THE DRAWINGS

In order to fragment and destroy stones or other concretions in remote locations within the body, an endoscope and other instruments must maneuver through tortuous paths to achieve proper positioning for diagnostic and operative procedures. In some cases, EHL probes are threaded through bends as sharp as between 90 and 120 degrees, and even up to 180 degrees. It can be extremely difficult to thread conventional EHL probes through these tortuous paths partially because of a lack of sufficient stiffness in the lithotripsy probe and their geometric shape that typically include square or slightly beveled edges. Moreover, conventional scopes and catheters often develop creases or "wrinkles" on the inner walls of their lumens due to the tortuous bends and frictional forces created by the lumen materials that cause the edges of the probes to become lodged or wedged in the scope or catheter lumens. Further, sharp or squared off edges of conventional laser fibers, ultrasound wands, and mechanical (ballistic) lithotripter probes can easily scrape or perforate the delicate body lumens they are threaded through.

The present disclosure is directed to invasive EHL probes that may be safely threaded through veins, arteries, ureters, and/or scope or catheter lumens to be positioned less than one millimeter or directly adjacent to concretions in remote locations within a patient. Generally, implementations of the disclosed EHL probes include rounded features positioned at leading surfaces of the EHL probe. These rounded features at the leading surfaces of the EHL probe typically come into contact with interior walls of veins, arteries, ureters, and/or scope lumens when the EHL probe is threaded through a patient's body. The rounded features reduce frictional forces with the interior walls, thereby reducing the formation of frictional forces in the creases and wrinkles in the inner walls of the veins, arteries, ureters, and/or scope or catheter lumens, as well as being less traumatic to tissue. The rounded features may further be coated with hydrophilic compounds to further reduce frictional forces. Coatings that could be used are commercially available formulations supplied by companies such as Biomet in Oakville Ontario, Biocoat in Horsham Pa., or Surface Solutions Group in Chicago Ill.

Additionally, implementations of the disclosed EHL probes may comprise one or more ports that allow liquid from the surrounding fluid environment to flow into the probe tip without the need to inject saline or other liquid for irrigation through a port into the probe tip to create the desired hydraulic effect. There is no need to force fluid into the tip with these implementations, thereby allowing for a smaller probe shaft diameter as there is no need to include a separate channel to force irrigant through the channel and into the tip.

Figure 26A:
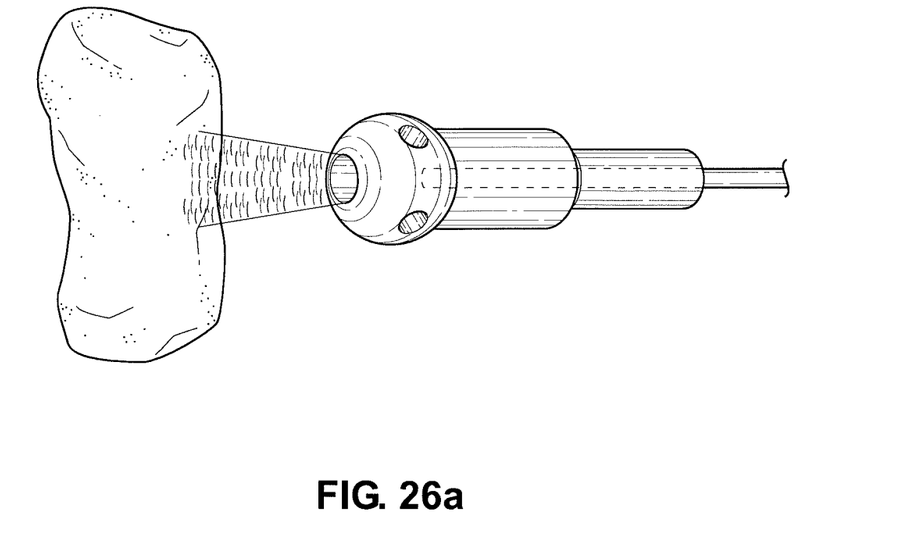
FIGS. 26a and 26b are diagrams illustrating example shockwaves created by some implementations of an EHL probe.
Figure 26B:
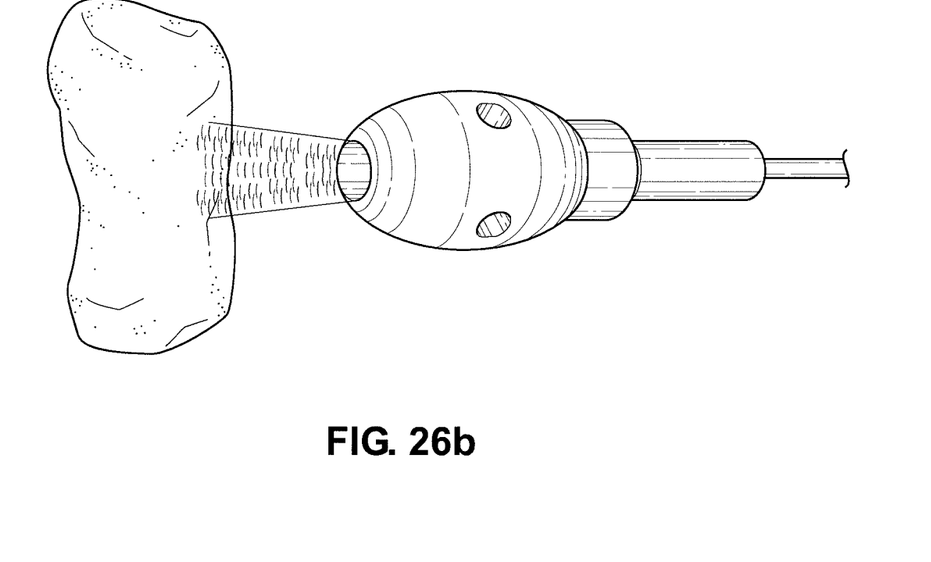

When an electric arc occurs between electrodes positioned in the interior region of the EHL probe, a gaseous bubble forms within the interior region. The gaseous bubble rapidly expands and contracts back on itself, thereby creating a pressure wave (a shockwave) in the liquid. The shockwave exits the interior region through an aperture at a distal end of the EHL probe and is focused against a stone or concretion positioned directly against to the EHL probe. Because the EHL probe is positioned directly against the stones or concretions, the potential to damage tissue adjacent to the stone or concretions is reduced when compared to conventional EHL probes that may not be positioned directly adjacent to the stone or concretion. Example shockwaves that the described EHL probes may create are shown in FIGS. 26a and 26b.

FIGS. 1-5 illustrate one implementation of an invasive EHL probe 100. The EHL probe includes a lithotripter tip body 102 that may comprise metal, plastic, or "glass" like materials that provide a smooth surface free or substantially free from burrs, noticeable grooves or protrusions. The lithotripter tip body 102 may be coated or plated with, but not limited to, copper, silver, or gold, for example. In some implementations, the metal is stainless steel, the circumference of the rounded tip body is equidistant from its center, has a radius of approximately 0.4 mm-1.0 mm, and the rounded tip is polished to give it a smooth surface.

The lithotripter tip body 102 defines at least a rounded portion 104 and a cylindrical portion 106. The rounded portion 104 is positioned at a distal end of the EHL probe 100 and the cylindrical portion 106 is positioned adjacent to the rounded portion 104. In some implementations, the rounded portion 104 may be donut shaped as shown in FIGS. 1-5, circular shaped as shown in FIGS. 6-10, or bead shaped as shown in FIGS. 11-15 so longus a leading surface of the EHL probe 100 presents a rounded surface to inner walls of a vein, artery, and/or lumen as the probe is threaded through a body of a patient.

A radius 108 of the rounded portion 104 is greater than a radius 110 of the cylindrical portion 106. Because the rounded portion 104 may extend farther from the lithotripter tip body 102 than the remainder of the lithotripter tip body 102, the rounded portion 104 is more likely to come into contact with inner walls of a vein, artery, and/or lumen as the EHL probe 100 is threaded through a body of a patient and positioned directly against a stone or concretion. It will be appreciated that the rounded portion 104 of the lithotripter tip body 102 reduces or eliminates the frictional forces that can cause creases or "wrinkles" to develop on the inner walls of a vein, artery, and/or lumen, and is less traumatic to the tissue.

In some implementations, the diameter of the rounded portion 104 is 1.5 millimeters or less. However, the size of the rounded portion 104 may be larger based on available lumen, endoscope, or the body area being accessed.

The lithotripter tip body 102 defines an interior region 112 with an aperture 114 positioned at the rounded portion 104 of the lithotripter tip body 102. In some implementations, the aperture 114 is flush with the rounded portion 104 of the lithotripter tip body 102 to reduce an amount of friction that the surface of the EHL probe 100 may cause as it is threaded through a vein or artery.

The lithotripter tip body 102 defines one or more ports 116 that are in communication with the interior region 112. The ports 116 are configured to provide a pathway to allow a liquid such as saline into the interior region 112. In some implementations, the ports 116 are between 0.007 and 0.014 inches in width or diameter.

Figure 1:
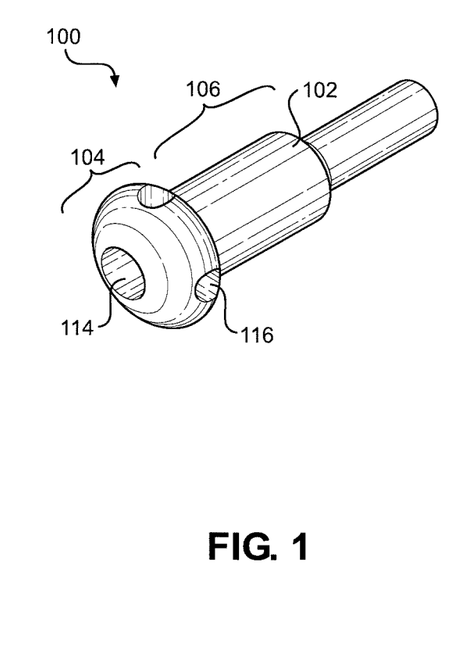
FIG. 1 is a perspective view of one implementation of an electrohydraulic lithotripsy probe (EHL probe).
Figure 2:
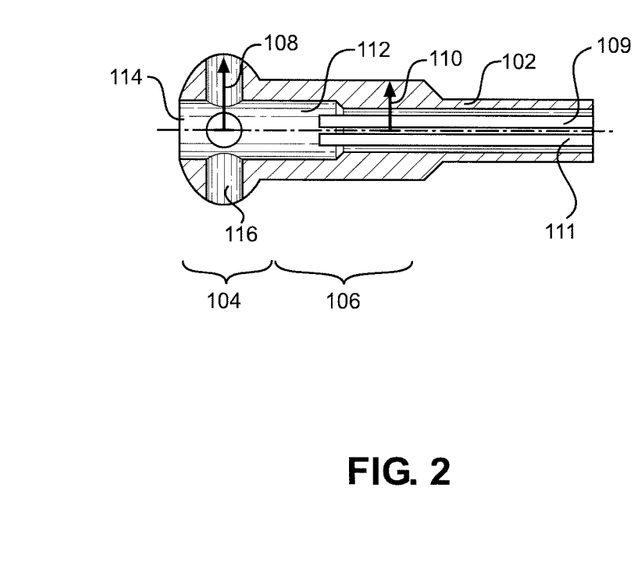
FIG. 2 is a cross-sectional side view of the EHL probe of FIG. 1.
Figure 3:
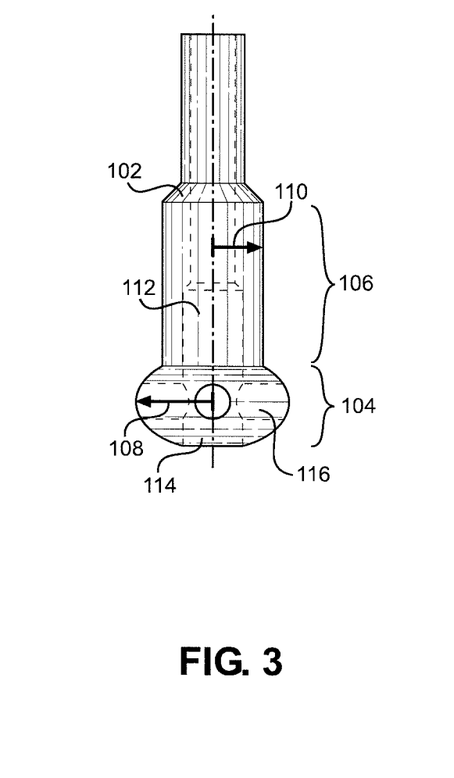
FIG. 3 is a side view of the EHL probe of FIG. 1.
Figure 4:
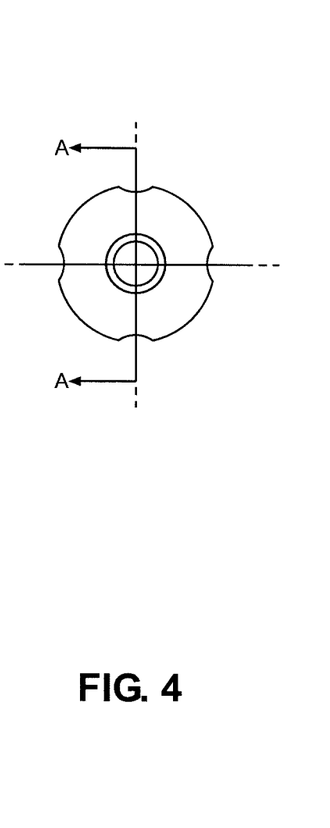
FIG. 4 is a front view of the EHL probe of FIG. 1.
Figure 5:
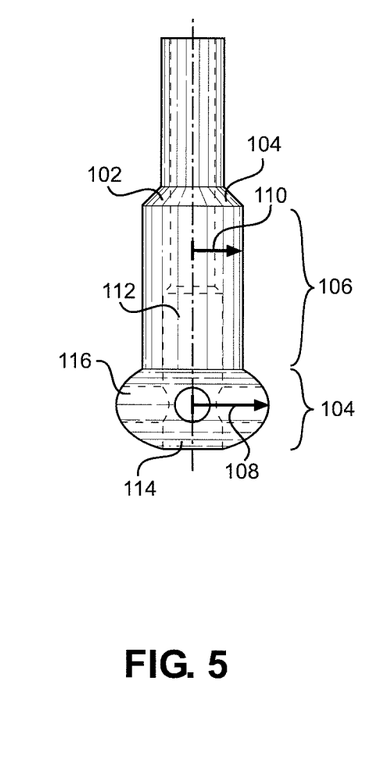
FIG. 5 is a top view of the EHL probe of FIG. 1.
Figure 6:
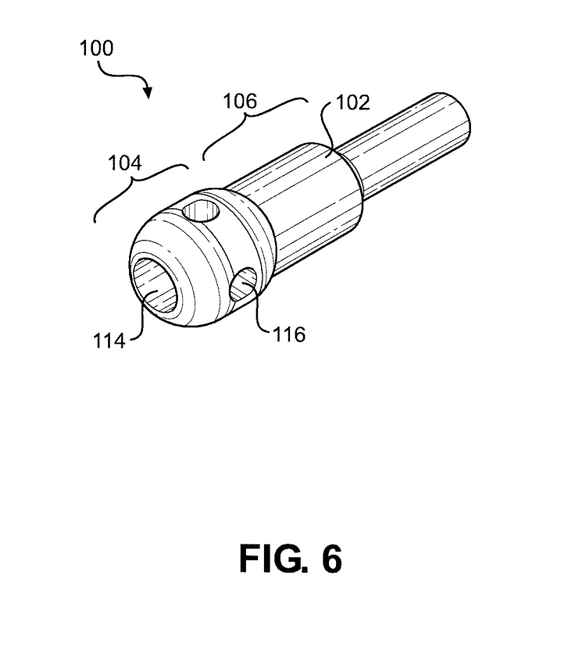
FIG. 6 is a perspective view of another implementation of an EHL probe.
Figure 7:
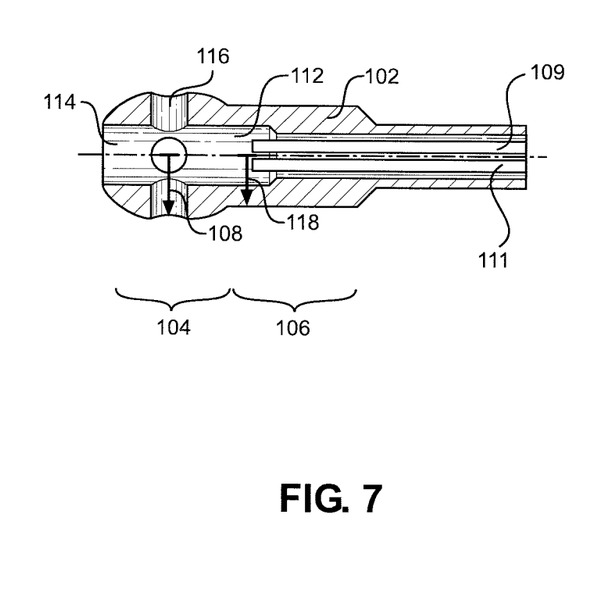
FIG. 7 is a cross-sectional side view of the EHL probe of FIG. 6.
Figure 8:
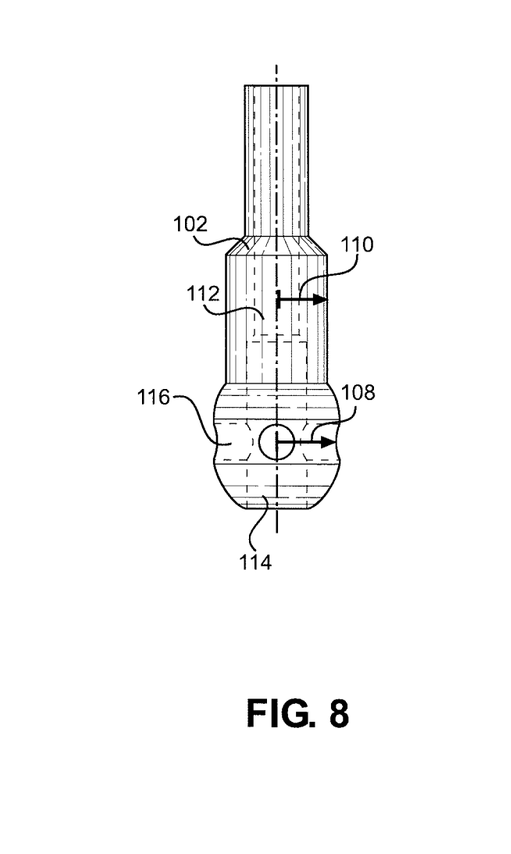
FIG. 8 is a side view of the EHL probe of FIG. 6.
Figure 9:
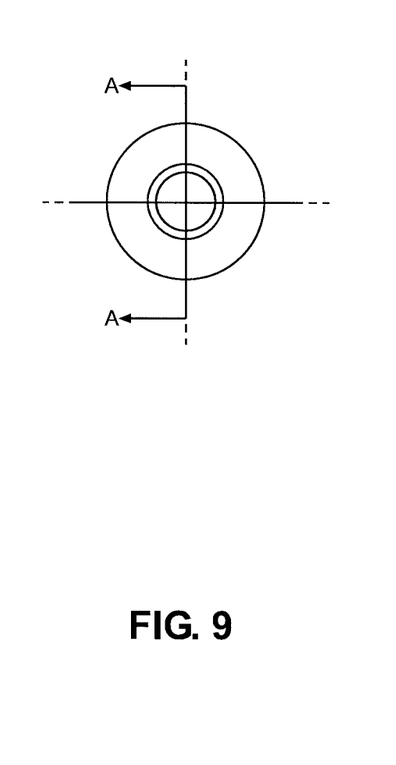
FIG. 9 is a front view of the EHL probe of FIG. 6.
Figure 10:
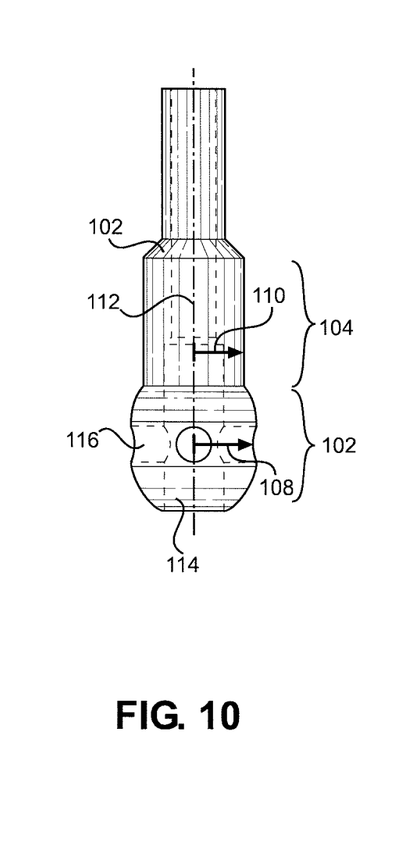
FIG. 10 is a top view of the EHL probe of FIG. 6.
Figure 11:
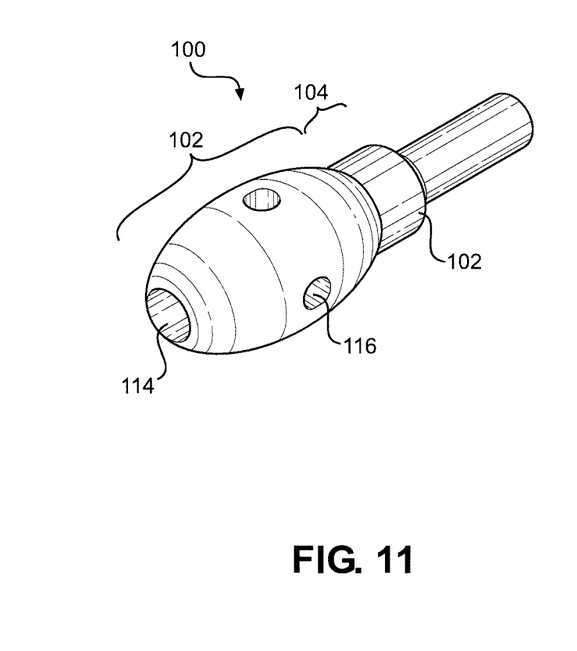
FIG. 11 is a perspective view of another implementation of an EHL probe.
Figure 12:
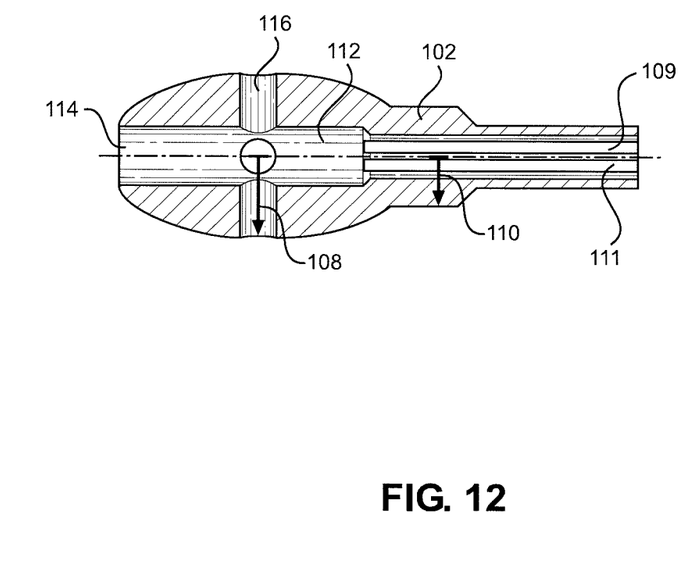
FIG. 12 is a cross-sectional side view of the EHL probe of FIG. 11.
Figure 13:
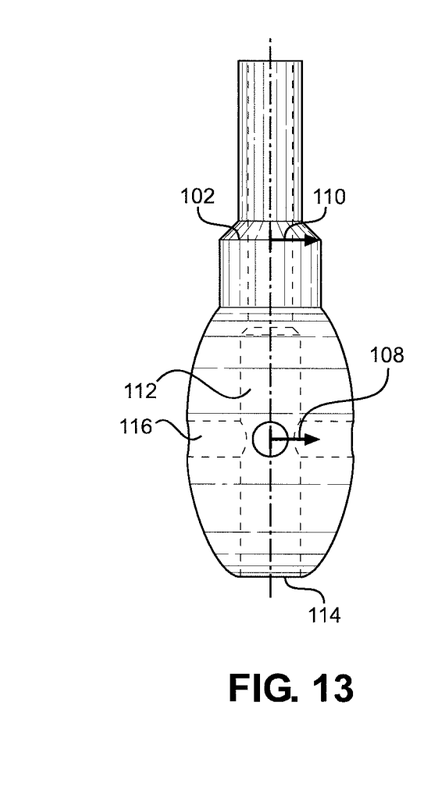
FIG. 13 is a side view of the EHL probe of FIG. 11.
Figure 14:
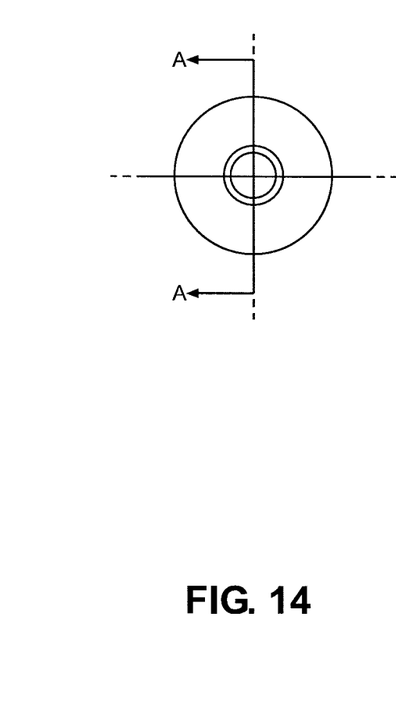
FIG. 14 is a front view of the EHL probe of FIG. 11.
Figure 15:
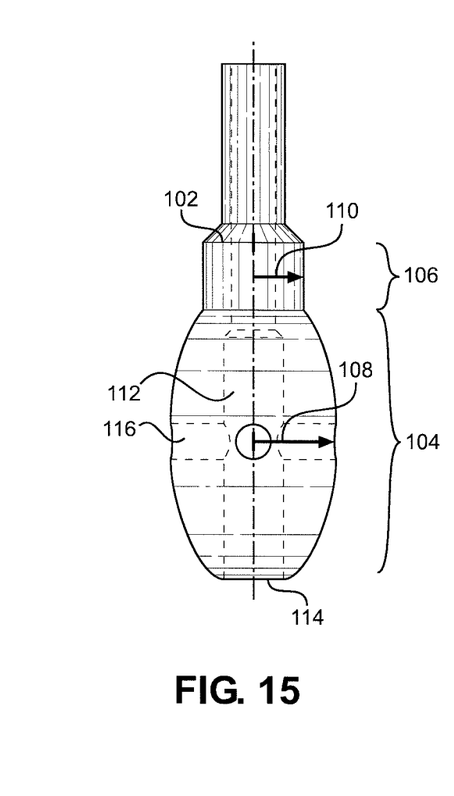
FIG. 15 is a top view of the EHL probe of FIG. 11.
Figure 16:
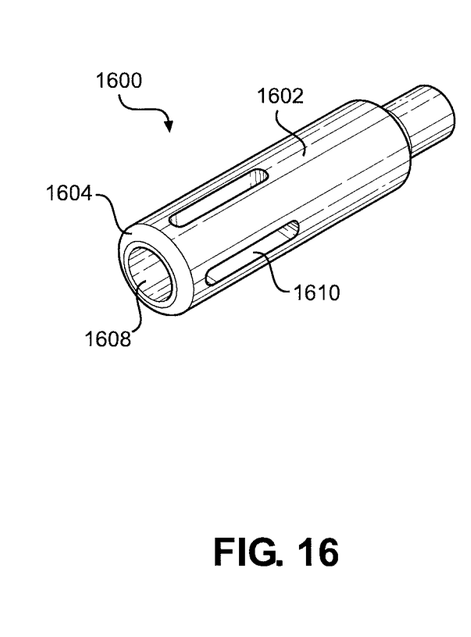
FIG. 16 is a perspective view of another implementation of an EHL probe.
Figure 17:
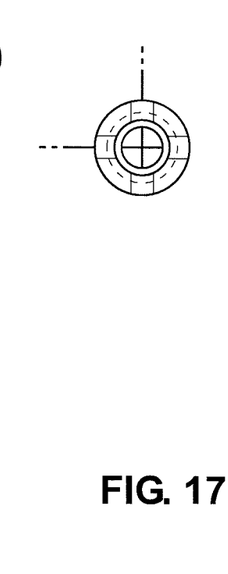
FIG. 17 is a front view of the EHL probe of FIG. 16.
Figure 18:
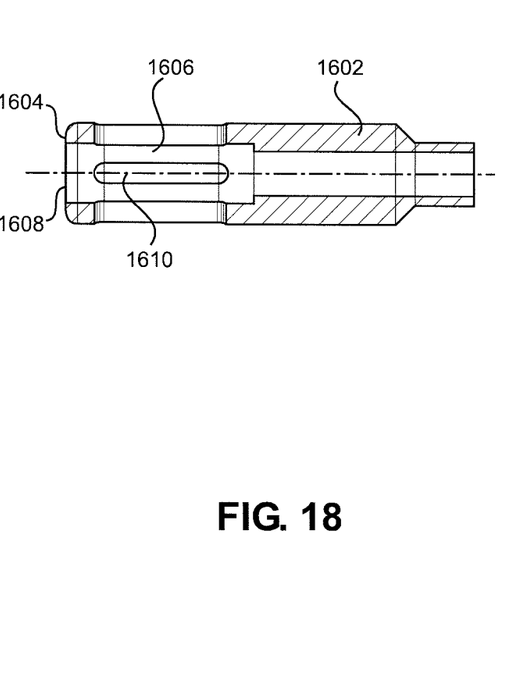
FIG. 18 is a side view of the EHL probe of FIG. 16.
Figure 19:
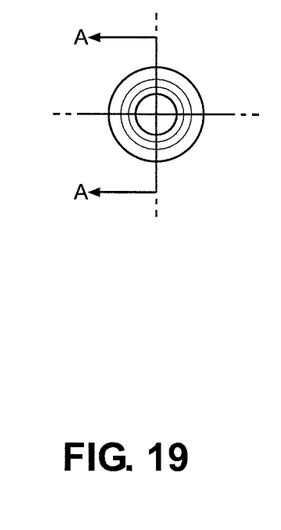
FIG. 19 is a rear view of the EHL probe of FIG. 16.

A first electrode 109 and a second electrode 111 are positioned within the interior region 112 of the EHL probe 100. In some implementations, the first or second electrodes may be a conductive version of the rounded tip, or two separate conductors residing within the tip. As known in the art, the first and second electrodes are coupled with an electrical source, such as an electrohydraulic generator (AUTOLITH® generator, supplied by Northgate Technologies Inc.), used to charge the first electrode to one polarity and the second electrode to an opposite polarity.

When the first electrode 109 is charged to a first polarity and the second electrode 111 is charged to a second, opposite polarity, a discharge of electricity occurs between the first and second electrodes (an electrical arc) when the potential between the first and second electrodes reaches the breakdown voltage for the media separating the electrodes.

When the interior region 112 of the EHL probe includes liquid such as saline, an electrical arc between the first and second electrodes 109, 111 causes a gaseous bubble in the interior region 112. The gaseous bubble rapidly expands and contracts back on itself. As the gaseous bubble contracts, a pressure wave (a shockwave) is created in the liquid within the interior region 112. The shockwave exits the interior region 112 at the aperture 114 positioned at the distal end of the EHL probe 100 where it impacts a stone or concretion positioned directly adjacent to the EHL probe 100.

A strength of an EHL shockwave when it impacts a concretion is a function of a distance between the concretion and the EHL probe that created the shockwave. The further away from the concretion the EHL probe is, the weaker the shockwave becomes when it impacts the concretion. Conventional EHL probes require a distance of at least 2 mm between the concretions and the EHL probe so that the pressure bubble has adequate space to form. However, with the EHL probes 100 of the present disclosure, the EHL probe 100 may be positioned directly against the concretion, thereby providing a stronger shockwave to impact the concretion when compared to conventional EHL probes. This is possible because the fluid that enters the probe tip through the port conducts the spark and the inside of the probe tip has sufficient space allow the bubble to form within the EHL probe 100. As the bubble escapes from the distal end of the EHL probe 100, the interior region 112 of the EHL probe 100 restricts a shockwave to reduce an amount of lateral pressure caused by the expanding and contracting "bubble" and directs the shockwave towards the aperture 114 at the distal end of the EHL probe 100. Accordingly, the body of the EHL probe 100 limits any unintended lateral forces from being projected to surrounding tissue, and directs the shockwave directly to a surface of the concretion.

Another implementation of an EHL probe 1600 is shown in FIGS. 16-20. The EHL probe 1600 includes a cylindrically shaped lithotripter tip body 1602. Similar to the EHL probes described above, a leading edge 1604 of the lithotripter tip body 1602 is rounded to reduce or eliminate frictional forces that can cause creases or "wrinkles" to develop on inner walls of veins, arteries, and/or ureter when the EHL probe 1600 is threaded through veins, arteries, and/or ureter.

The lithotripter tip body 1602 defines an interior region 1606 and an aperture 1608 in communication with the interior region 1606. The aperture 1608 is positioned at a distal end of the lithotripter tip body 1602 and in some implementations is flush with the rounded leading edge 1604 of the lithotripter tip body 1602.

The lithotripter tip body 1602 additionally defines one or more ports 1610 in communication with the interior region 1606. The ports 1610 provide a pathway to inject a liquid such as saline into the interior region 1606. In some implementations the ports 1610 may be elongated ovals such as those shown in FIGS. 16-20, wherein in other implementations the ports 1608 may be other shapes such as the circular ports 1608 shown in FIGS. 21-25.

Figure 20:
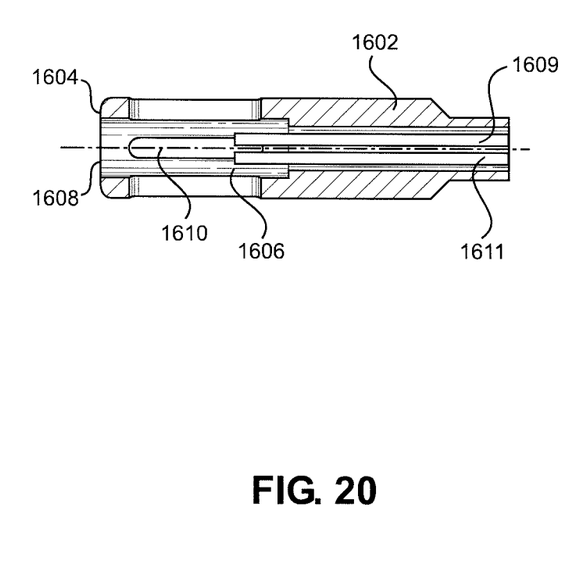
FIG. 20 is a cross-sectional side view of the EHL probe of FIG. 16.
Figure 21:
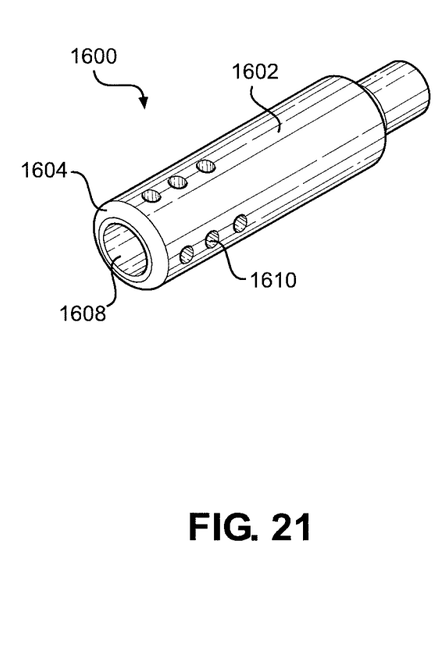
FIG. 21 is a perspective view of another implementation of an EHL probe.
Figure 22:
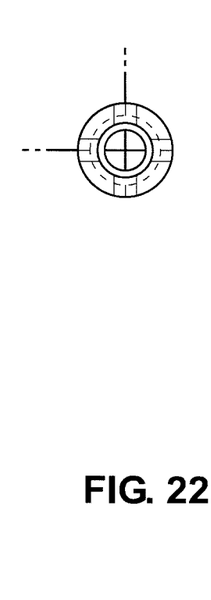
FIG. 22 is a front view of the EHL probe of FIG. 21.
Figure 23:
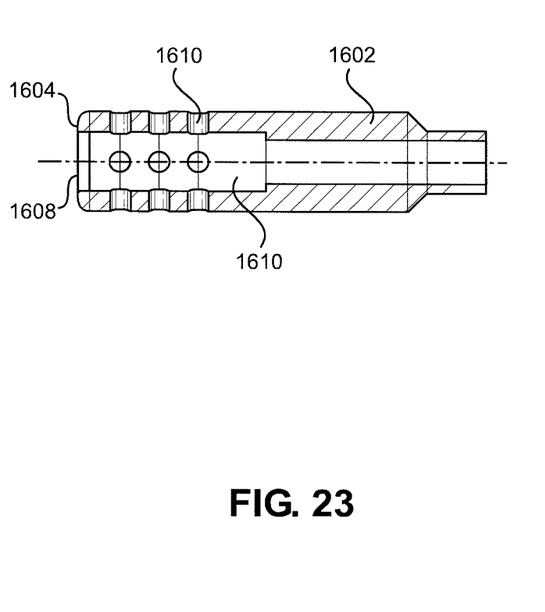
FIG. 23 is a side view of the EHL probe of FIG. 21.
Figures 24, 25:
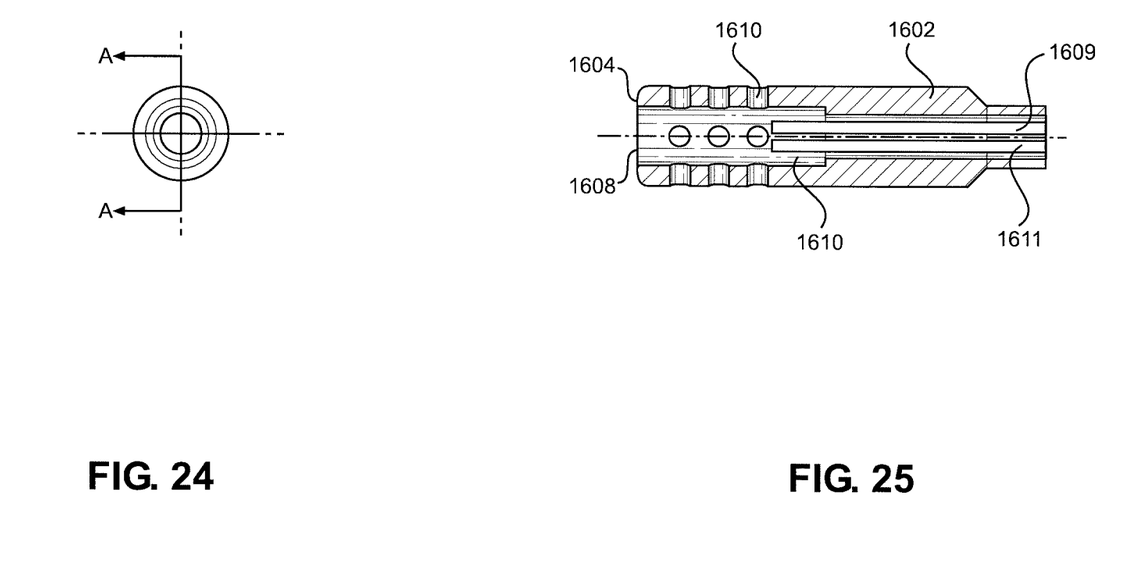
FIG. 24 is a rear view of the EHL probe of FIG. 21
FIG. 25 is a cross-sectional side view of the EHL probe of FIG. 21.

A first electrode 1609 and a second electrode 1611 are positioned within the interior region 1606 of the EHL probe 1600. As known in the art, the first and second electrodes are coupled with an electrical source, such as an electrohydraulic generator (AUTOLITH®, supplied by Northgate Technologies Inc.), used to charge the first electrode to one polarity and the second electrode to an opposite polarity.

When the first electrode 1609 is charged to a first polarity and the second electrode 1611 is charged to a second, opposite polarity, a discharge of electricity occurs between the first and second electrodes (an electrical arc) when the potential between the first and second electrodes reaches the breakdown voltage for the media separating the electrodes.

When the interior region 1606 of the EHL probe includes liquid such as saline, an electrical arc between the first and second electrodes 1609, 1611 causes a gaseous bubble in the interior region 1606. The gaseous bubble rapidly expands and contracts back on itself. As the gaseous bubble contracts, a pressure wave (a shockwave) is created in the liquid within the interior region 1606. The shockwave exits the interior region 1606 at the aperture 1608 positioned at the distal end of the EHL probe 1600 where it impacts a stone or concretion positioned directly adjacent to the EHL probe 1600. In some implementations, the interior region 1606 is configured to restrict lateral pressure from the shockwave that forms in the interior region 1606 and to focus the shockwave to the distal end of the EHL probe 1600.

A strength of an EHL shockwave when it impacts a concretion is a function of a distance between the concretion and the EHL probe that created the shockwave. The further away from the concretion the EHL probe is, the weaker the shockwave becomes when it impacts the concretion. Conventional EHL probes require a distance of at least 2 mm between the concretions and the EHL probe. However, with the EHL probes 1600 of the present disclosure, the EHL probe 1600 may be positioned directly against the concretion, thereby providing a stronger shockwave to impact the concretion when compared to conventional EHL probes.

Figure 27:
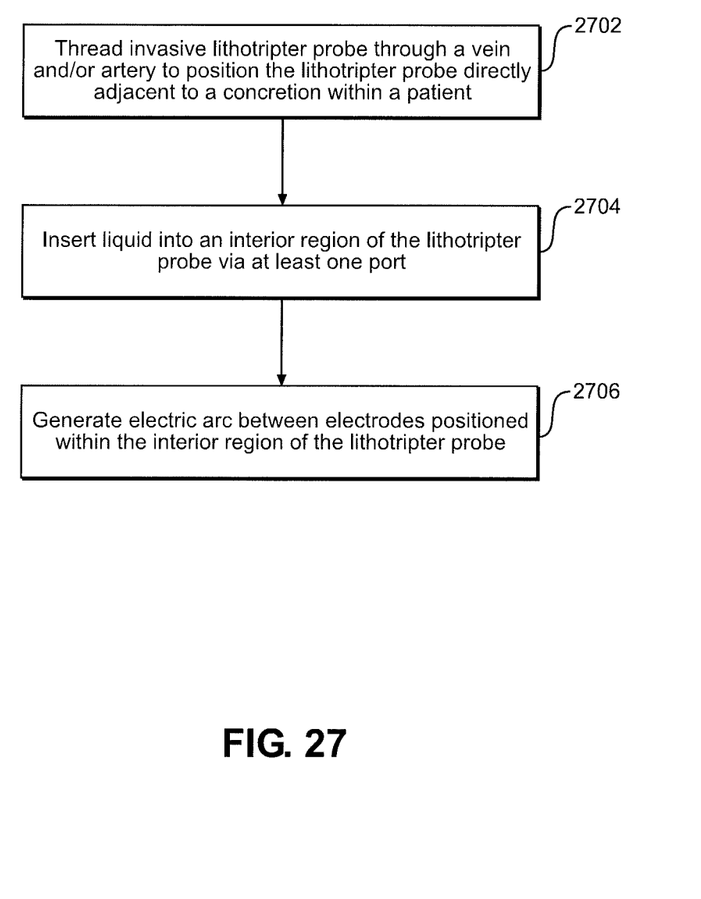
FIG. 27 is a flow chart of a method for using a rounded EHL probe with ports.

FIG. 27 is a flow chart of a method for using a rounded EHL probe with ports. The method begins at step 2702 with threading an invasive lithotripter probe through a human vein or artery to position the lithotripter probe directly adjacent to a concretion within a patient. In some implementations, the invasive lithotripter probe may be a probe such as those described above where the lithotripter probe comprises a lithotripter tip body that defines at least a cylindrical portion and a rounded portion, the rounded portion is positioned at a distal end of the lithotripter tip, the cylindrical portion is positioned adjacent to the rounded portion, and a radius of the rounded portion is greater than a radius of the cylindrical portion.

At step 2704, a liquid such as saline is inserted or flows into the interior region of the lithotripter tip body via at least one port that provides a path for liquid to flow into the interior region.

At step 2706, an electric arc is generated between a first electrode and a second electrode positioned within an interior region of the lithotripter probe tip, wherein the electric arc causes a gaseous bubble to form within the interior region of the lithotripter probe and a resulting shockwave to travel from the interior region through an aperture at the distal end of the lithotripter tip and to impact the concretion positioned directly adjacent to the lithotripsy probe.

FIGS. 1-27 illustrate implementations of invasive EHL probes that may be safely threaded through veins, arteries, and/or ureter to be positioned directly adjacent to concretion in remote locations within a patient. Rounded features at leading surfaces of the EHL probes reduce friction forces with interior veins arteritis, and/or ureter, thereby reducing the formation of creases and wrinkles in the inner walls of the veins, arteries, and/or ureter. The disclosed EHL probes may also include ports that are utilized to inject a liquid such as saline into an interior region of the EHL probe.

It is intended that the foregoing detailed description be regarded as illustrative rather than limiting, and that it be understood that it is the following claims, including all equivalents, that are intended to define the spirit and scope of this invention.

The invention claimed is:

1. A lithotripter tip configured for use with an invasive lithotripter probe, the lithotripter tip comprising:
    a lithotripter tip body dimensioned and configured to be threaded through a human vein or artery of a patient and delivered to a position directly adjacent to a concretion within the patient, wherein the lithotripter tip body defines an interior region in communication with an aperture at a distal end of the lithotripter tip body; and
    a first electrode and a second electrode positioned within the interior region of the lithotripter tip body;
    wherein the first and second electrodes are positioned within the interior region of the lithotripter tip body such that an electric arc between the ends of the first and second electrodes causes a gaseous bubble to form within the interior region of the lithotripter tip body and a shockwave that forms as a result of the gaseous bubble to travel out of the aperture at the distal end of the lithotripter tip body and to impact the concretion positioned directly adjacent to the lithotripter tip;
    wherein an exterior of the lithotripter tip body defines at least a cylindrical portion and a rounded portion, wherein the rounded portion is positioned at the distal end of the lithotripter tip body, the cylindrical portion is positioned adjacent to the rounded portion, and a radius of the rounded portion is greater than a radius of the cylindrical portion; and
    wherein the exterior of the lithotripter tip body defines at least one side port at the rounded portion of the exterior that is in communication with the interior region of the lithotripter tip body, where the at least one side port is configured to receive a liquid from an environment exterior to the lithotripter tip body and provide a path for the liquid to flow from the environment and into the interior region.

2. The lithotripter tip of claim 1, wherein the interior region is configured to restrict lateral pressure from the shockwave that forms in the interior region and to focus the shockwave to the distal end of the lithotripter tip.

3. The lithotripter tip of claim 1, wherein the rounded portion is donut shaped.

4. The lithotripter tip of claim 1, wherein the rounded portion is circular shaped.

5. The lithotripter tip of claim 1, wherein the rounded portion is bead shaped.

6. A lithotripter tip configured for use within an invasive lithotripter probe, the lithotripter tip comprising:
    a lithotripter tip body dimensioned and configured to be threaded through a human vein or artery of a patient and delivered to a position directly adjacent to a concretion within the patient, wherein the lithotripter tip body defines an interior region in communication with an aperture at a distal end of the lithotripter tip body and the lithotripter tip body defines at least one side port in communication with the interior region that is configured to receive a liquid from an environment exterior to the lithotripter tip body and provide a path for the liquid to flow from the environment and into the interior region of the body; and
    a first electrode and a second electrode positioned within the interior region of the lithotripter tip;
    wherein the first and second electrodes are positioned within the interior region such that when liquid from the at least one side port is within the interior region and an electric arc occurs between the ends of the first and second electrodes, a gaseous bubble forms within the interior region and a resulting shockwave travels out of the aperture at the distal end of the lithotripter tip body and impacts the concretion positioned directly adjacent to the lithotripter tip body;

wherein an exterior of the lithotripter tip body defines at least a cylindrical portion and a rounded portion, wherein the rounded portion is positioned at the distal end of the lithotripter tip body, the cylindrical portion is positioned adjacent to the rounded portion, and a radius of the rounded portion is greater than a radius of the cylindrical portion; and wherein the exterior of the lithotripter tip body defines the at least one side port at the rounded portion of the exterior.

7. The lithotripter tip of claim 6, wherein the interior region is configured to restrict lateral pressure from the shockwave that forms in the interior region and to focus the shockwave to the distal end of the lithotripter tip.

8. The lithotripter tip of claim 6, wherein each of the at least one side port is positioned at the rounded portion of the exterior of the lithotripter tip body.

9. The lithotripter tip of claim 6, wherein the rounded portion is donut shaped.

10. The lithotripter tip of claim 6, wherein the rounded portion is circular shaped.

11. The lithotripter tip of claim 6, wherein the rounded portion is bead shaped.

\* \* \* \* \*